United States Patent
Vernin (12)

(10) Patent No.: US 6,200,572 B1
(45) Date of Patent: Mar. 13, 2001

(54) CAPSULE CONTAINING PLANT EXTRACTS AND MICROENCAPSULATED ESSENTIAL OILS

(76) Inventor: Jacques Vernin, 9, boulevard Charles Gay, P-77000 Melun (FR)

( * ) Notice: Subject to any disclaimer, the term of this patent is extended or adjusted under 35 U.S.C. 154(b) by 0 days.

(21) Appl. No.: 09/423,193

(22) PCT Filed: May 12, 1998

(86) PCT No.: PCT/FR98/00943

§ 371 Date: Oct. 28, 1999

§ 102(e) Date: Oct. 28, 1999

(87) PCT Pub. No.: WO98/51320

PCT Pub. Date: Nov. 19, 1998

(30) Foreign Application Priority Data

May 12, 1997 (FR) .................................................. 97 05767

(51) Int. Cl.$^7$ .......................... A61K 39/385; A61K 7/00; A61K 2/14
(52) U.S. Cl. ...................... 424/195.1; 424/401; 424/489
(58) Field of Search ................................ 424/195.1, 401, 424/489

(56) References Cited

U.S. PATENT DOCUMENTS 4,172,072 * 10/1979 Ashmead ............................. 530/345

5,082,974 * 1/1992 Hashimoto et al. ................... 568/41

FOREIGN PATENT DOCUMENTS

2572935 * 5/1986 (FR) .
WO 97/01347 1/1997 (WO) .

OTHER PUBLICATIONS

Patent Abstracts of Japan, Vo. 95, No. 5, Oct. 2, 1995—JP 07 039312, Mitsuzo.

Database WPI Section Ch, Week 8450, Derwent Publications XP002052969, JP 59193818.

* cited by examiner

*Primary Examiner*—David M. Naff
*Assistant Examiner*—Michael V. Meller
(74) *Attorney, Agent, or Firm*—Burns, Doane, Swecker, & Mathis, L.L.P.

(57) ABSTRACT

A composition which can be used in the cosmetic and therapeutic fields comprises one or more plant extracts with defined active ingredient titers, one or more individually microencapsulated essential oils, a buffer mixed with the microencapsules of essential oils and one or more pharmaceutically or cosmetically acceptable excipients which is contained within a capsule.

7 Claims, No Drawings

CAPSULE CONTAINING PLANT EXTRACTS AND MICROENCAPSULATED ESSENTIAL OILS

BACKGROUND OF THE INVENTION

1. Field of the Invention

The present invention relates to a new composition which can be used in the pharmaceutical, dietetic and cosmetic fields, and more particularly a new composition combining plant extracts of defined titers and essential oils providing enhanced effects.

2. Description of the Related Art

For many years, various natural substances have been used because of their pharmacological and cosmetological properties. Plants are sometimes used directly, simply dried and packaged in bulk after harvest, cut to different degrees, or alternatively ground, in order to make infusions, or sprayed at room or cold temperature. In all cases, the preservation of dry plants, in bulk or treated as indicated above, can only be achieved for a relatively short period of time because preservation for a period of a few months, or even a few weeks, causes loss of their properties which are often linked to components which are very volatile or sensitive to oxidation.

Fine pulverization of a plant increases the surface area of contact between the content of the plant cells and the ambient air and promotes their impairment, to the extent that it is often necessary to preserve the powders under vacuum or under an inert gas atmosphere in order to preserve their properties. Furthermore, for example in the case of grinding for the preparation of powders, it is often necessary to use grinders cooled with liquid nitrogen in order to avoid heating which may cause the loss of the volatile substances.

Among the various known forms of presentation, dry extracts, as well as essential oils, also called plant essences are often used.

Dry extracts are generally obtained by extracting the dry plant with water, alone or mixed with ethanol in variable quantities. The extracted juices are concentrated and then dried and mixed with excipients intended to facilitate the drying and the preservation. Depending on the techniques used, it is possible to obtain between about 0.15 g and 1 g of dry extract for 2 g of dry plant.

The dry extracts prepared by conventional techniques are generally hygroscopic and their preservation is difficult.

The plant extracts may also be incorporated, as adjuvants, into compositions, as described for example in patent FR-A-2,688,137 relating to moisturizing cosmetic compositions.

Aromatic plants contain on average 2% by weight of an odorous substance, also called "essence", which is a natural secretion of the plant organism. Once extracted from the plant, generally by steam distillation, it is called "essential oil".

As a result of their chemical composition, most essential oils have antiseptic and bactericidal properties. Depending on the botanical species, they may have specific properties which have been the subject of a very large number of studies for years, and which have allowed their use for external use and for internal use, in the cosmetic and therapeutic fields. Essential oils are more particularly used in aromatherapy for the treatment of various infectious states, either as principal therapeutic agent, or as adjuvant. For example, patent FR-A-2,670,386 describes a cosmetic composition containing an essential oil from basil intended to serve as repellent against certain insects.

However, on the one hand, the commercially available plant extracts generally exhibit insufficient stability, which further decreases their efficacy, and, on the other hand, it is known that essential oils are extremely sensitive to oxidation, and their preservation should therefore be carried out in the absence of air. Furthermore, essential oils should be used with care, and it is considered that it is necessary to avoid administering them separately, but that on the contrary they should be mixed with various excipients because of the unpleasant sensations which they cause in contact with the mucous membranes in the mouth.

The result is that the efficacy of treatments is greatly limited, and, even in the case of gelatin capsules, knowing that it is often necessary to administer more than 10 g of plant per day in order to obtain a favorable result, the user would have to take more than 50 gelatin capsules per day in order to be able to hope to obtain an effective treatment.

The same applies to the other conventional forms, such as infusions, decoctions or tinctures. Thus, by using conventional techniques, useful results can only be hoped to be obtained by taking each day quantities at least equal to 6 infusions or 60 g of tincture at ⅕ or of homeopathic stock tincture at ⅒ of fresh plant, containing alcohol at a high titer, of the order of 60 volumes. It is of course impossible to envisage taking such quantities. Likewise, the essential oils formulated by conventional techniques can only be used diluted in alcoholic solutions with high titers.

Patent FR-A-2,572,935 describes a composition for dietary use comprising a substrate consisting of a plant powder, containing an essential oil obtained from the same plant. The essential oil should be heated so as to be incorporated into the substrate, and the result is a volatilization of most of the oil, and a degree of instablilty of the composition.

A need therefore exists for effective and stable compositions which can be used in small quantities and which allow simple administration of the essential active ingredients of plants.

SUMMARY OF THE INVENTION

The subject of the present invention is new compositions which can be used in the therapeutic, dietetic and cosmetic fields, comprising plant extracts with defined active ingredient titers, and essential oils, in the form of a mixture, if necessary, with pharmaceutically or cosmetically acceptable excipients, and exhibiting excellent stability over time.

The new compositions according to the present invention are preferably provided in the form of gelatin capsules or of capsules administrable by the oral route. They may also be provided in a form administrable by the topical route, for example a gel.

According to a preferred embodiment of the invention, the essential oils used in the compositions are in the form of microcapsules.

The microcapsules contain an essential oil and are preferably combined with a buffer. The buffer used in the invention is mixed with the microcapsules and generally consists of a bicarbonate or a hydrogen carbonate, a phosphate buffer or alternatively ethylenediaminetetraacetic acid. Preferably, sodium bicarbonate is used. The buffer facilitates gastric tolerance and makes it possible, in addition, to avoid having to carry out an enteric coating of the gelatin capsules containing the composition of the invention. A mixture of microcapsules containing various essential oils may be used in accordance with the present invention.

The size of the microcapsules used in the present invention is generally between 25 $\mu$m and 0.5 mm, and preferably between 50 μm and 300 μm. The polymers used to form the wall of the microcapsules may be chosen from those commonly used in pharmaceutical and cosmetic techniques. According to the invention, gelatin, a gum arabic or a gum tragacanth is preferably used, separately or in the form of a mixture.

In accordance with the invention, it is possible to prepare, for example, gelatin capsules or capsules containing between 0.05 g and 0.50 g of dry extract of defined titer and between 0.05 g and 0.50 g of microcapsules of essential oil, per gelatin capsule or capsule. These quantities are not limiting and may vary as a function of the size of the gelatin capsules or of the capsules.

The compositions of the invention also make it possible to advantageously combine dry extracts with defined titers of active ingredients from several plants with one or more microencapsulated and buffered essential essences from other plants.

In the case of application in dermatology or in cosmetology, the compositions of the invention may be easily adapted to an external use by incorporating, into an appropriate excipient, liquid or dry plant extracts, of defined titers or otherwise, and microcapsules of essential oils. Thus, it is possible to prepare compositions in accordance with the present invention in the form of a gel for topical application. An appropriate excipient may be, for example, a gel such as a Carbopol gel.

The compositions in accordance with the present invention possess various advantages relative to the conventional forms of presentation of natural substances. In particular, they are completely assimilable and exhibit an improved bioavailability, an excellent stability over time without the need to preserve them under very rigorous conditions of temperature and relative humidity, and they potentiate the effects of the natural active ingredients used. Furthermore, they preserve the integrity of the essential oils with respect to their volatilization and their oxidation, and the microencapsulation prevents the risks of a reaction between the constituents of the associated essential oils, where appropriate. Finally, the tolerance, in particular the gastric tolerance, is improved, even in the case of a composition containing mixtures of microcapsules, whereas the administration of a mixture of essential oils generally causes an irritant effect for the mucous membranes.

More particularly, the compositions according to the present invention offer an immediate action due to the microcapsules of essential oils, supplemented by a prolonged action derived from the plant extracts.

Thus, the trials carried out with various compositions in accordance with the present invention have shown that a gelatin capsule containing dry plant extracts with defined active ingredient titers and microcapsules of essential oils have an activity equivalent to that of 10 to 30 conventional gelatin capsules of dry plants.

The following examples illustrate the invention in greater detail without limiting the scope thereof. In these 15 examples, the parts are given by weight unless otherwise stated.

EXAMPLE 1

A rosemary dry extract concentrated at 1:8 and of defined titer, that is to say 0.15 g of dry extract per 1.2 g of plant, is prepared by a known technique (aqueous-alcoholic extraction, concentration at 35°, and then drying under vacuum).

Moreover, using a technique of micro-encapsulation by coacervation, microcapsules (gelatin content: 20%) containing a buffered rosemary essence (0.15 g of essence per 3.35 g of plant) are prepared. The buffer used is sodium bicarbonate.

After mixing the microcapsules, the buffer and the powder of rosemary dry extract of defined titer, in a Frogerais cube mixer, a composition is obtained which is incorporated into gelatin capsules (gelatin capsule No. 1) using an apparatus for filling by leveling.

The composition of the gelatin capsule is therefore:

| | |
|---|---|
| Rosemary dry extract of defined titer (1:8) | 0.15 g |
| Microcapsules of buffered rosemary essence | 0.15 g |

A gelatin capsule of the composition thus prepared corresponds to 4.55 g of dry plant, that is to say about 22 to 23 gelatin capsules of plant powder according to a conventional technique.

This composition exhibits properties of digestive tonic promoting digestion allowing its use as a dietary supplement.

EXAMPLE 2

Using the same preparation technique as in Example 1, a powder of burdock dry extract of defined titer (1:5) is prepared in the form of a mixture with a powder of hop dry extract of defined titer (1:5).

Moreover, microencapsulated buffered thyme essences and microencapsulated buffered mint essences are prepared.

The whole is mixed and a 400 mg gelatin capsule having the following composition is thus obtained:

| | |
|---|---|
| Burdock dry extract of defined titer (1:5) | 0.10 g |
| Hop dry extract of defined titer (1:5) | 0.10 g |
| Microcapsules of buffered thyme essence | 0.10 g |
| Microcapsules of buffered mint essence | 0.10 g |

A gelatin capsule of the composition thus prepared corresponds to 2.8 g of dry plant, that is to say about 10 gelatin capsules of plant powder according to a conventional technique.

This composition exhibits properties of hepatic tonic and skin antiseptic allowing its use in the therapeutic and dietetic field for the treatment of skin manifestations.

EXAMPLE 3

A composition in the form of a skin gel for dermatological use by topical application is prepared which has the following composition:

| | |
|---|---|
| Aqueous-alcoholic extract of harpagophytum | 40 g |
| Aqueous-alcoholic extract of juniper berries | 10 g |
| Microencapsulated buffered | 2 g |

| -continued | |
|---|---|
| Eucalyptus citriodora essence Special excipient for instant absorption | 50 g |

A skin gel having anti-inflammatory properties is thus obtained.

What is claimed is:

1. A composition which can be used in cosmetic, and therapeutic fields, comprising a combination of
    one or more plant extracts with defined active ingredient titers,
    one or more individually microencapsulated essential oils,
    a buffer mixed with the microcapsules of essential oils such that the buffer surrounds the microcapsules,
    one or more pharmaceutically or cosmetically acceptable excipients; and
    wherein said composition is contained within a capsule.

2. The composition according to claim 1, wherein the size of the microcapsules is between 25 $\mu$m and 0.5 mm.

3. The composition according to claim 1, wherein the buffer is sodium bicarbonate.

4. The composition according to claim 1, wherein the capsule contains between 0.05 g and 0.50 g of dry extract of defined titer and between 0.05 g and 0.50 g of microcapsules of essential oil.

5. The composition according to claim 2, wherein the capsule contains between 0.05 g and 0.50 g of dry plant extract of defined titer and between 0.05 g and 0.50 g of microcapsules of essential oil.

6. The composition according to claim 3, wherein the capsule contains between 0.05 g and 0.50 g of dry plant extract of defined titer and between 0.05 g and 0.50 g of microcapsules of essential oil.

7. The composition according to claim 1, wherein the size of the microcapsules is between 25 microns and 0.5 mm, and the buffer is sodium bicarbonate.

* * * * *